(12) United States Patent
Micele, Jr. et al.

(10) Patent No.: US 7,011,425 B2
(45) Date of Patent: Mar. 14, 2006

(54) LUMINARY PRODUCT

(75) Inventors: Anthony G. Micele, Jr., deceased, late of Kenosha, WI (US); by Melissa D. Morris, legal representative, Racine, WI (US); Francois P. Delcourt, Chicago, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/632,164

(22) Filed: Aug. 1, 2003

(65) Prior Publication Data

US 2005/0024859 A1 Feb. 3, 2005

(51) Int. Cl.
*F21V 9/16* (2006.01)

(52) U.S. Cl. .................. 362/161; 362/332; 362/333; 362/84; 362/806

(58) Field of Classification Search .............. 362/161, 362/84, 806, 173, 179, 182, 312, 315, 332, 362/333; 431/289

See application file for complete search history.

(56) References Cited

U.S. PATENT DOCUMENTS

| | | |
|---|---|---|
| 1,275,871 A | 8/1918 | Dodds et al. |
| 1,660,760 A | 2/1928 | Murphy |
| 2,000,985 A | 5/1935 | Quinlan et al. ............ 240/2.25 |
| 2,001,377 A | 5/1935 | Candy, Jr. ..................... 67/22 |
| 2,050,151 A | 8/1936 | Baumer ....................... 240/13 |
| RE20,434 E | 7/1937 | Barrett, Jr. et al. ............. 67/21 |
| 2,137,707 A | 11/1938 | Wade et al. ................... 67/21 |
| 3,126,682 A | 3/1964 | Krance ......................... 53/30 |
| 3,286,492 A | 11/1966 | Frazier, Jr. .................... 67/21 |
| 3,586,473 A | 6/1971 | Galloway et al. ........... 431/126 |
| 3,674,733 A | 7/1972 | Ayella ....................... 260/30.6 |
| 3,696,675 A | 10/1972 | Gilmour ...................... 73/295 |
| 3,741,711 A | 6/1973 | Bryant ....................... 431/125 |
| 3,760,968 A | 9/1973 | Amberg et al. ........... 215/12 R |
| 3,822,459 A | 7/1974 | Amberg et al. ........... 29/208 B |
| 3,829,348 A | 8/1974 | Speigel et al. ............... 161/16 |
| 3,867,625 A | 2/1975 | Whalen ....................... 240/13 |

(Continued)

FOREIGN PATENT DOCUMENTS

GB            1 033 320            6/1966

(Continued)

OTHER PUBLICATIONS (Exhibit 1) Copy of digital color photograph of two GLADE® candles commercially sold by S.C. Johnson & Son, Inc. (1 page).

(Continued)

*Primary Examiner*—Sandra O'Shea
*Assistant Examiner*—Anabel Ton (57) ABSTRACT

A decorated luminary product includes a candle holder containing a candle, wherein at least one of the inner surface and the outer surface of the candle holder has a hammered texture such that light passing through the candle holder varies substantially as a result of variation of refraction of the light. A decorative web of a heat-shrinkable polymer may be heat shrunk to conform to the outer surface of the candle holder. The web is decorated with an ink or pigmentation to cooperate with light and/or heat emitted by burning the candle, so as to provide a pleasing visual effect when the candle is burned, while the hammered texture of the candle holder causes variations in the refraction of light emitted from the candle, causing further visual effects. The refraction of light caused by the hammered texture of the candle holder also provides aesthetically pleasing effects when the candle is unlit, due to variations in the image on the web resulting from variation in the light observed passing through the candle holder.

24 Claims, 4 Drawing Sheets

U.S. PATENT DOCUMENTS

| | | | | |
|---|---|---|---|---|
| 3,948,445 | A | 4/1976 | Andeweg | 239/53 |
| 3,979,000 | A | 9/1976 | Karabedian | 215/12 R |
| 4,028,118 | A | 6/1977 | Nakasuji et al. | 106/21 |
| 4,034,131 | A | 7/1977 | Rhoads | 428/35 |
| 4,038,446 | A | 7/1977 | Rhoads | 428/35 |
| 4,067,949 | A | 1/1978 | Karabedian | 264/230 |
| 4,069,934 | A | 1/1978 | Karabedian | 215/12 R |
| 4,071,597 | A | 1/1978 | Karabedian | 264/230 |
| 4,187,276 | A | 2/1980 | Amberg | 264/515 |
| 4,190,168 | A | 2/1980 | Jacques | 215/12 R |
| 4,225,049 | A | 9/1980 | Inoue | 215/12 R |
| 4,248,030 | A | 2/1981 | Heckman | 53/397 |
| 4,285,746 | A | 8/1981 | DePuy et al. | 156/79 |
| RE30,805 | E | 11/1981 | Rhoads | 428/35 |
| 4,304,547 | A | 12/1981 | Buzil | 431/126 |
| 4,358,955 | A | 11/1982 | Rait | 73/295 |
| 4,416,714 | A | 11/1983 | Hoffmann | 156/86 |
| 4,428,790 | A | 1/1984 | Diaz | 156/86 |
| 4,436,777 | A | 3/1984 | Karpiloff | 428/36 |
| 4,463,861 | A | 8/1984 | Tsubone et al. | 215/12 R |
| 4,483,890 | A | 11/1984 | Beery et al. | 428/7 |
| 4,507,077 | A | 3/1985 | Sapper | 431/228 |
| 4,524,778 | A | 6/1985 | Brown, Jr. et al. | 128/736 |
| 4,591,887 | A | 5/1986 | Arbree et al. | 346/200 |
| 4,608,284 | A | 8/1986 | Roales | 428/35 |
| 4,608,323 | A | 8/1986 | Zaborney | 429/167 |
| 4,696,844 | A | 9/1987 | Spector | 428/46 |
| 4,704,843 | A | 11/1987 | Owen et al. | 53/450 |
| 4,708,817 | A | 11/1987 | Dudnick | 252/301.16 |
| 4,720,301 | A | 1/1988 | Kito et al. | 106/21 |
| 4,725,462 | A | 2/1988 | Kimura | 428/29 |
| 4,732,810 | A | 3/1988 | Kito et al. | 428/402.2 |
| 4,741,909 | A | 5/1988 | Guthrie | 426/107 |
| 4,759,090 | A | 7/1988 | Sachetti | 5/482 |
| 4,818,214 | A | 4/1989 | Ronnback | 431/35 |
| 4,818,215 | A | 4/1989 | Taga | 431/126 |
| 4,844,957 | A | 7/1989 | Hoffman | 428/34.7 |
| 4,947,299 | A | 8/1990 | Lin | 362/161 |
| 4,961,797 | A | 10/1990 | Doheny | 156/85 |
| 4,977,002 | A | 12/1990 | Hoffman | 428/34.7 |
| 4,996,087 | A | 2/1991 | Rebstock | 428/11 |
| 5,059,895 | A | 10/1991 | Cataldi et al. | 324/104 |
| 5,083,251 | A | 1/1992 | Parker | 362/255 |
| 5,108,805 | A | 4/1992 | Gerard | 428/34.9 |
| 5,129,979 | A | 7/1992 | Nakayama et al. | 156/294 |
| 5,154,600 | A | 10/1992 | Sylvestre | 431/253 |
| 5,167,154 | A | 12/1992 | Lee | 73/295 |
| 5,172,937 | A | 12/1992 | Sachetti | 283/81 |
| 5,175,142 | A | 12/1992 | Dervieux et al. | 512/4 |
| 5,190,609 | A | 3/1993 | Lin et al. | 156/85 |
| 5,223,003 | A | 6/1993 | Tucholski et al. | 29/623.4 |
| 5,223,958 | A | 6/1993 | Berry | 359/43 |
| 5,252,155 | A | 10/1993 | Nowicki et al. | 156/84 |
| 5,264,995 | A | 11/1993 | McKee | 362/161 |
| 5,282,651 | A | 2/1994 | Alonso | 283/117 |
| 5,323,652 | A | 6/1994 | Parker | 73/295 |
| 5,330,815 | A | 7/1994 | Brudermann et al. | 428/68 |
| 5,403,635 | A | 4/1995 | Hoffman | 428/34.7 |
| 5,437,410 | A | 8/1995 | Babasade | 239/55 |
| 5,447,248 | A | 9/1995 | Rodriguez et al. | 215/366 |
| 5,482,373 | A | 1/1996 | Hutchinson | 374/141 |
| 5,520,385 | A | 5/1996 | Quigley et al. | 273/57.2 |
| 5,548,493 | A | 8/1996 | Young | 362/84 |
| 5,562,959 | A | 10/1996 | Wood et al. | 428/34.9 |
| 5,569,511 | A | 10/1996 | Spector | 428/11 |
| 5,590,779 | A | 1/1997 | Ramsey | 206/459.1 |
| 5,605,230 | A | 2/1997 | Marino, Jr. et al. | 206/534 |
| 5,605,765 | A | 2/1997 | Rudick | 428/484 |
| 5,654,552 | A | 8/1997 | Toombs | 250/462.1 |
| 5,683,762 | A | 11/1997 | Banschick | 428/4 |
| 5,786,578 | A | 7/1998 | Christy et al. | 219/720 |
| 5,798,184 | A | 8/1998 | Sasa et al. | 428/484 |
| 5,833,349 | A | 11/1998 | Apple | 362/84 |
| 5,849,046 | A | 12/1998 | Bailey | 29/623.5 |
| 5,849,375 | A | 12/1998 | Smith et al. | 428/34.5 |
| 5,866,236 | A | 2/1999 | Faykish et al. | 428/195 |
| 5,879,151 | A | 3/1999 | Schultz et al. | 431/291 |
| 5,879,496 | A | 3/1999 | Bright et al. | 156/86 |
| 5,882,774 | A | 3/1999 | Jonza et al. | 428/212 |
| 5,894,089 | A | 4/1999 | Ogawa | 73/295 |
| 5,922,158 | A | 7/1999 | Culp et al. | 156/86 |
| 5,927,959 | A | 7/1999 | Johnson | 431/125 |
| 5,932,685 | A | 8/1999 | Mori et al. | 528/272 |
| 5,948,257 | A | 9/1999 | Custer et al. | 210/500.26 |
| 5,951,278 | A * | 9/1999 | Young et al. | 431/291 |
| 5,953,170 | A | 9/1999 | Glancy | 359/896 |
| 5,962,158 | A | 10/1999 | Yoppolo et al. | 429/93 |
| 5,962,368 | A | 10/1999 | Poole | 503/227 |
| 5,985,387 | A | 11/1999 | Mori et al. | 428/34.9 |
| 6,003,287 | A | 12/1999 | Ballestrazzi et al. | 53/546 |
| 6,020,823 | A | 2/2000 | DeCicco | 340/691.2 |
| 6,036,024 | A | 3/2000 | Seidler | 206/780 |
| 6,045,894 | A | 4/2000 | Jonza et al. | 428/212 |
| 6,048,423 | A | 4/2000 | Barrash et al. | 156/86 |
| 6,057,012 | A | 5/2000 | Culp et al. | 428/34.9 |
| 6,059,564 | A * | 5/2000 | Morris | 431/291 |
| 6,079,975 | A | 6/2000 | Conover | 431/288 |
| 6,113,720 | A | 9/2000 | Fresnel | 156/85 |
| 6,113,996 | A | 9/2000 | Amon et al. | 428/34.9 |
| 6,165,234 | A | 12/2000 | Kanakkanatt | 44/275 |
| 6,181,446 | B1 | 1/2001 | Cox et al. | 359/3 |
| 6,183,829 | B1 | 2/2001 | Daecher et al. | 428/64.1 |
| 6,197,430 | B1 | 3/2001 | Asakura et al. | 428/480 |
| 6,270,866 | B1 | 8/2001 | Okuda et al. | 428/35.1 |
| 6,344,250 | B1 | 2/2002 | Arthurs | 428/34.9 |
| 6,436,496 | B1 | 8/2002 | Rackovan et al. | 428/34.9 |
| 6,554,447 | B1 | 4/2003 | Kotary et al. | 362/161 |
| 6,554,448 | B1 * | 4/2003 | Carpenter et al. | 362/161 |
| 6,827,474 | B1 * | 12/2004 | Clapper | 362/557 |
| 2001/0040800 | A1 | 11/2001 | Carpenter et al. | 362/166 |
| 2001/0043467 | A1 * | 11/2001 | Carpenter et al. | 362/84 |
| 2001/0043469 | A1 | 11/2001 | Carpenter et al. | 362/161 |
| 2003/0029544 | A1 | 2/2003 | Noguchi et al. | 156/85 |
| 2003/0068453 | A1 | 4/2003 | Kong | 428/35.2 |

FOREIGN PATENT DOCUMENTS

| | | |
|---|---|---|
| GB | 1 528 193 | 10/1978 |
| GB | 2 358 193 A | 7/2001 |
| JP | 7-216384 | 8/1995 |
| JP | 8-218092 | 8/1996 |
| JP | 10-102086 | 4/1998 |
| WO | WO 99/16608 | 4/1999 |
| WO | WO 99/36248 | 7/1999 |
| WO | WO 99/36258 | 7/1999 |
| WO | WO 99/36477 | 7/1999 |
| WO | WO 99/36478 | 7/1999 |
| WO | WO 99/36808 | 7/1999 |
| WO | WO 99/36812 | 7/1999 |
| WO | WO 00/07046 | 7/2001 |

OTHER PUBLICATIONS (Exhibit 2) Copy of digital color photograph of two GLADE® candles commercially sold by S.C. Johnson & Son, Inc. (1 page).

(Exhibit 3) Copy of digital color photograph of a prototype candle with blue-colored wrap (1 page).

(Exhibit 4) Copy of digital color photograph of a candle bearing religious graphics (1 page).

(Exhibit 5) Copy of digital color photograph of a candle bearing heart- and tree-shaped graphics (1 page).

(Exhibit 6) Copy of digital color photograph of a candle bearing "CANDLE LITE" graphics (1 page).

(Exhibit 7) Copy of digital color photograph of a candle bearing "aroma therapy" graphics (1 page).
(Exhibit 8) Copy of digital color photograph of a candle bearing "aroma therapy" graphics (1 page).
(Exhibit 9) Copy of digital color photograph of a candle bearing cartoon graphics (1 page).
(Exhibit 10) Copy of digital color photograph of a candle bearing Halloween graphics (1 page).
(Exhibit 11) Copy of digital color photograph of "Green Glass Votive" marked as "Product 3300954" (1 page), as posted on Internet World Wide Web page entitled "Pierre Deux Home Furnishings—Glassware", by Pierre Deux; <http://www.pierredeux.com/gethfglassware.cfm>.
(Exhibit 12) Copy of Internet World Wide Web page entitled "Pierre Deux Home Furnishings—Glassware", by Pierre Deux; <http://www.pierredeux.com/gethfglassware.cfm>(9 pages).
(Exhibit 13) Copy of Internet World Wide Web page entitled "Heart Votive Holder from Candles & More", by Bobby's Craft Boutique Inc.; <http://www.craftcave.com/candle/heartvotive.shtml>(1 page).
(Exhibit 14) Copy of Internet World Wide Web page entitled "Stained Glass Garden—Textured-clears glass", by Stained Glass Garden; <http;//www.stainedglassgarden.com/textured_clear_b.html> (7 pages).
(Exhibit 15) Copy of Internet World Wide Web page entitled "Spectrum Hammered—Glass From Sample Box", by Stained Glass Garden; <http://www.stainedglassgarden.com/hammered.html> (3 pages).
(Exhibit 16) Copy of Internet World Wide Web page entitled "Glass Hammered Heart TeaLight Candle Holders-Heart Votive Holder-Tea Light CandleHolders-Grandpa's General Store", by Grandpa's General Store; <http://www.grandpasgeneral.com/canholdtl2.html> (4 pages).
(Exhibit 17) Copy of promotional document entitled "ARC International: tailor-made on an industrial scale", by ARC International, 62510 Arques, France; document marked "Imprimé par C&P R.C. Saint-Omer 5772802 74B AN 541/01 9274014" (42 pages).
(Exhibit 18) Copy of promotional document entitled "Liquor Premium", by ARC International North America, Millville, NJ 08332; document marked "Imprimé par C&P R.C. Saint-Omer 5772802 74B AN 534/98 9005298" (4 pages).
(Exhibit 19) Copy of promotional document entitled "Success Stories", by ARC International North America, Millville, NJ 08332; document marked "Imprimé par C&P R.C. Saint-Omer 5772802 74B AN 157/01 9225133" (6 pages).
(Exhibit 20) Copy of promotional document entitled "Special Markets Collection", by ARC International North America, Millville, NJ 08332; document marked "Imprimé par C&P R.C. Saint-Omer 5772802 74B AN 483/02 9343958" (28 pages).
(Exhibit 21) Copy of promotional document entitled "Catalogue Arcoroc", by Verrerie Cristallerie d'Arques, J.G. Durand & Cie, 62510 Arques, France; document marked "Imprimé par C&P R.C. Saint-Omer 5772802 74B PB 72/99 9049461" (143 Pages).
(Exhibit 22) Copy of promotional document entitled "ChromaZone®—Color Changing—Temperature Sensitive—Slurries Pigments Coatings Inks Paints & Injection Molding", by Davis Liquid Crystals, Inc., 15021 Wicks Blvd., San Leandro, CA 94577 (4 pages).
(Exhibit 23) Copy of promotional document entitled "ChromaZone®—Applications Guide", by Davis Liquid Crystals, Inc., 15021 Wicks Blvd., San Leandro, CA 94577 (1 page).
(Exhibit 24) Copy of promotional document entitled "ChromaZone®—Formulation Notes", by Davis Liquid Crystals, Inc., 15021 Wicks Blvd., San Leandro, CA 94577 (1 page).
(Exhibit 25) Copy of promotional document entitled "ChromaZone®—Injection Molding Powder, Extrusion and Cast Films", by Davis Liquid Crystals, Inc., 15021 Wicks Blvd., San Leandro, CA 94577 (1 page).
(Exhibit 26) Copy of promotional document entitled "JPS Packaging—Questions Commonly Asked About Thermochromics" (1 page).
(Exhibit 27) Copy of promotional document entitled "JPS Packaging—Temperature Chart—Chromic Color Changing Regular Type" (1 page).
(Exhibit 28) Copy of promotional document entitled "JPS Packaging—Thermochromatic Inks—General Information and Considerations" (1 page).
(Exhibit 29) Copy of article entitled "Giant Birefringent Optics in Multilayer Polymer Mirrors", Weber et al., Science, vol. 287, no. 5462, pp. 2451-2456, Mar. 31, 2000 (12 pages).
(Exhibit 30) Copy of promotional document entitled "Kromacorp International—General Presentation—Aug. 1999—Kromathermic Temperature Sensitive Inks" (3 pages).
(Exhibit 31) Copy of promotional document entitled "Productivity Profile—K is for cool", reprinted from Beverage World, Feb. 1997 (1 page).
(Exhibit 32) Copy of International Search Report, dated Oct. 11, 2001, in International Appln. No. PCT/US 01/10460 (see U.S. Appl. No. 09/753,962, (7 pages).
(Exhibit 33) Copy of International Search Report, dated Oct. 9, 2001, in International Appln. No. PCT/US 01/10544 (see U.S. Appl. No. 09/729,288) (7 pages).
(Exhibit 34) Copy of International Search Report, dated Oct. 10, 2001, in International Appln. No. PCT/US 01/10461 (see U.S. Appl. No. 09/550,285, (8 pages).

* cited by examiner

LUMINARY PRODUCT

BACKGROUND OF THE INVENTION

1. Technical Field

Our invention, in general, relates to decorated luminary products, and more particularly to luminary products decorated by the use of transparent jars having a hammered texture forming an inner surface thereof, and also preferably including a decorative film wrapped around the jar. The hammered texture provides for refraction of the light emitted by, for example, a candle in the luminary product, in such a manner as to provide a varying light show as a result of the flickering of the candle flame.

2. Background Information

Luminary products come in many shapes, sizes, and designs. Such luminary products are typically wick based and burn a hydrocarbon-based fuel, and include such items as candles, oil lamps or lanterns.

In many cases, it is desirable to decorate the luminary products to improve their aesthetics, both when the luminary is unlit and when lit. However, it can be difficult and costly to decorate the outer surface of a luminary product or its holder. Also, many known techniques do not provide flexibility in production to rapidly and easily change the particular decorative design. This limits the ability to cost-effectively provide a variety of designs, or to tailor the designs to the desires of the consumer, or to a specific season, event, motif, holiday or the like, or to provide a product having a decorative effect which changes in accordance with whether the luminary is itself lit or unlit.

Therefore, a need exists for a luminary product capable of being cost-effectively manufactured with one of a variety of desired decorative designs that preferably changes in appearance when the luminary itself is burning. A further need exists that such variety of decorative luminary products be subject to production by a method that permits greater manufacturing flexibility and that simplifies the process of changing from one decorative design to another. Yet another need exists that such a decorative luminary product provide for an irregular or nonrepeating refraction of light through portions of the body of the luminary product to augment a visual effect when the luminary is burning.

It has long been known to encase candles in protective material. For example, U.S. Pat. No. 2,137,707 to Wade et al., relates to a process for packaging tapered candles in a seamless casing formed of a non-fibrous, cellulosic material. The casing may be transparent, translucent and/or colored. In one embodiment, the non-fibrous, cellulosic material is formed into a tube, which is wetted to soften the material for application to the candle. The diameter of the wet tube is substantially equal to the mean diameter of the tapered candle, and as the wet tube is pushed down onto the candle, or a mandrel having the same dimensions as the candle, it stretches as necessary to fit over the wider end of the candle. Then, the covered candle is dried, and the tube forms a protective casing that conforms closely to the shape of the candle and will retain the candle wax whether in a solid or melted state.

It has also been known to wrap candles in heat-shrinkable films for shipping and display. U.S. Pat. No. 3,126,682 to Krance teaches a method of wrapping candles. A tube of heat-shrinkable film material is loosely formed about the candle by shaping a web of the material about the candle with overlapping longitudinal edges. The wrapped candle is carried past a heat source, by which the material is heat shrunk around the candle while the tube is grasped just beyond each end of the candle. The material selected has at least the following two important characteristics: it will not shrink any further once it contacts the surface of the candle and it holds a high charge of static electricity, which causes it to cling when overlapped. Thus, the material is not heat sealed, but rather is held together statically around the candle after shrinking to a tight fit.

It has also been known to apply heat-shrinkable webs on various objects. For example, U.S. Pat. No. 3,829,348 to Spiegel et al. relates to decorating three-dimensional objects such as ornaments, glassware, or electric bulbs. The object is decorated by heat-shrinking a decorated tube or band of heat-shrinkable plastic about the object. The tube or band is decorated by applying precut patterns, silk screening, striping or the like, prior to application of the tube or band to the object to be decorated. The plastic is polyvinyl chloride (PVC) or polyethylene, which is uniaxially oriented, resulting in a 30–50% diametric shrinkage versus only a 2–10% height shrinkage of the tube, resulting in an intimate contact of the entire interior surface of the band or tube with the exterior surface of the decorated object.

Similarly, U.S. Reissue Pat. No. 20,434 to Barrett, Jr., teaches the preparation of a sanctuary candle, wherein the body of the candle is jacketed in a cylindrical transparent film of amorphous cellulose, which is fitted to the candle while it is still un-dried. It is taught that the film may be either clear or colored, and may be combined with a colored glass tube forming the outside of the assembly, which includes a bottom assembly and a cap.

There is a need in the art, however, for a candle holder that reacts with a candle flame so that the light emitted from the flame varies substantially as a result of variation of refraction of the light of the candle flame as the light passes through the glass candle holder.

SUMMARY OF THE INVENTION

Our invention relates to luminary products that provide an impression of changing or varying light, as the flame of the luminary product burns. Thus, as the inner surface of the novel candle holder, including such structures as chimneys, globes, jars, or other surrounding surfaces (hereinafter "candle holder"), is illuminated by the flame of a candle or light-emitting element, the light emanating from the flame appears to change as a result of light refraction resulting from the specially chosen candle holder. Moreover, the candle holder preferably includes a shrink-wrapped web about its outer surface that has a printed design, such that the printed design appears to change as the light refracts through the specially chosen candle holder.

Figure 4:
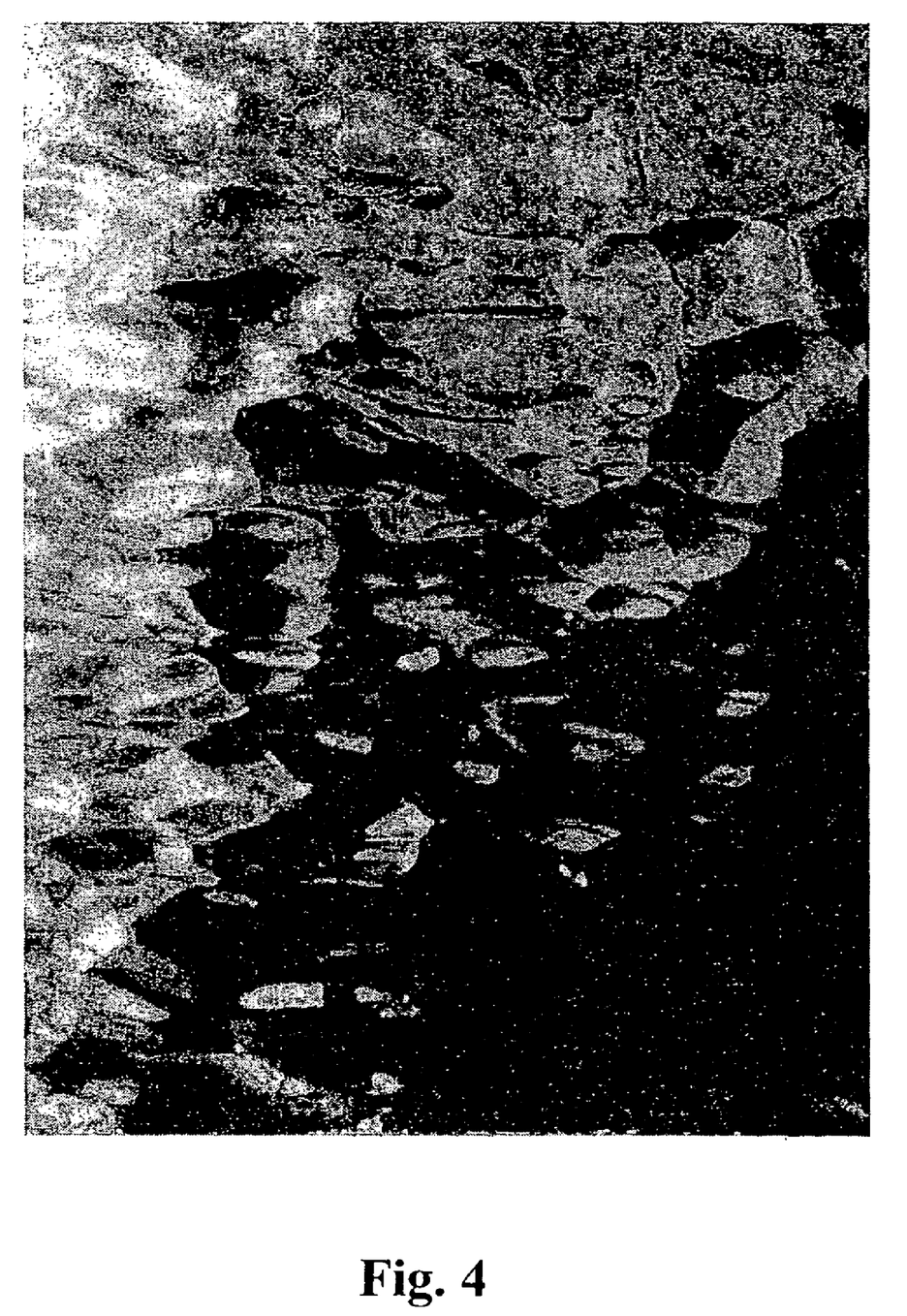
FIG. 4 is a plan view of an example of a hammered surface.

The specially chosen candle holder according to our invention includes an inner surface with a "hammered" texture. We understand the term "hammered" as used to describe the texture of a surface to be a term of art in at least, for example, the glass art or industry. For instance, "hammered" means glass textured by indentations which resembles a surface that has been beaten with a ball-peen hammer, or a surface texture similar to hammered brass or copper, that is, a texture having small, rounded-like, substantially smooth bumps. We intend these meanings to describe the hammered effect for all embodiments of our invention. One example of a hammered texture, available from Stained Glass Garden of Berkeley, Calif., is shown in FIG. 4.

Within this meaning of "hammered" and according to our invention, the hammered surface preferably is created by way of a variation in thickness of the candle holder so as to provide a visual impression that the surface has been subjected to a treatment resulting in changes of thickness of the candle holder and creating a surface that appears to have been subjected to a hammering operation, or an appearance similar to a surface that has been imperfectly smoothed by being hammered. As a result of the variations in thickness of the candle holder, the light emitted by the flame of the luminary product is subjected to variations in refraction, the effect of which variations are amplified by the flickering of the flame itself.

The hammered texture may be provided on one or both of the inner and outer surfaces of the candle holder, although the hammered texture is preferably provided only on the inner surface.

Most preferably, the inner surface of the candle holder has a texture that consists of a continuous depression (or relative thinness) bounding a plurality of mounds (or relative thickness), each of which generally extends towards the center of the candle holder so that from the viewpoint of the center of the candle holder each mound has a substantially convex appearance.

In our invention, the candle holder preferably comprises a transparent material such as glass or plastic, so that light can pass through the candle holder and be effected by the variations in refraction of light passing through the glass or plastic.

As previously mentioned, there is preferably applied to the outer surface of the candle holder a heat shrunk web upon which a design or indicia has been printed, painted, or otherwise applied. (However, it will be appreciated by one having ordinary skill that the heat shrunk web may be omitted from the outer surface of the candle holder.) The design or indicia may be applied as the sole layer of decoration, or may be part of a more complex decoration in which a number of layers of imprinted, drawn, or otherwise applied indicia or designs are present, using normal ink or paint either alone or in conjunction with thermochromatic ink, phosphorescent ink, or color-changing ink or paint.

For example, a heat-shrinkable film, prior to application to the outer surface of a candle holder, may be printed with a background layer, or a single design or pattern of conventional ink, and a second pattern may be applied over the first, in registry therewith so as to produce a desired pattern, to provide a specific effect upon heating of the heat-shrinkable film by the burning of the candle within the candle holder. The aesthetic effect of a flickering flame through such heat-shrinkable films is enhanced by virtue of the candle holder of a specific form or configuration, especially a candle holder having the hammered texture. This hammered texture on the inner surface of the candle holder provides a pleasing effect, as the light is refracted in differing patterns when it passes through the glass and is refracted differently at various points upon the glass surface.

Accordingly, in one aspect, a decorated luminary product comprises a candle, a candle holder suitable for containing the candle, the candle holder having an inner surface and an outer surface, and a web of a heat shrunk polymer encasing the outer surface of the candle holder. The web includes a decorative feature. At least one of the inner surface and the outer surface of the candle holder has a hammered texture and the decorative feature of the web is located so as to cooperate with light emitted by the candle in the candle holder to augment a visual effect when the candle is lit.

Another aspect of the invention relates to a decorated luminary product comprising a candle, a candle holder selected from the group consisting of chimneys, globes and jars, suitable for containing a candle, the candle holder having an inner surface and an outer surface, and a web of a heat shrunk polymer encasing the candle holder, the web including a decorative feature. At least one of the inner surface and the outer surface of the candle holder has a hammered texture and the decorative feature of the web is located so as to cooperate with light emitted by the candle in the candle holder to augment a visual effect when the candle is lit.

Yet another aspect of the invention relates to a luminary product comprising a combustible material and a glass jar containing the combustible material, which has been poured into the glass jar. The glass jar has an inner surface and an outer surface. At least one of the inner surface and the outer surface of the glass jar has a hammered texture such that light passing through the glass jar varies substantially as a result of variation of refraction of the light.

The novel luminaries obtained by the practice of this invention produce visual effects that are inexpensive, visually pleasing, change throughout the duration of the burning of the candle, and are capable of being provided with a large variety of designs, such as seasonal or holiday themes. This is particularly noticeable in the case of a burning candle, where the height of the candle flame varies as the candle is burned, changing the angle at which the light of the candle flame impinges upon the surface of the candle holder.

DETAILED DESCRIPTION OF THE PREFERRED EMBODIMENTS

Figure 1:
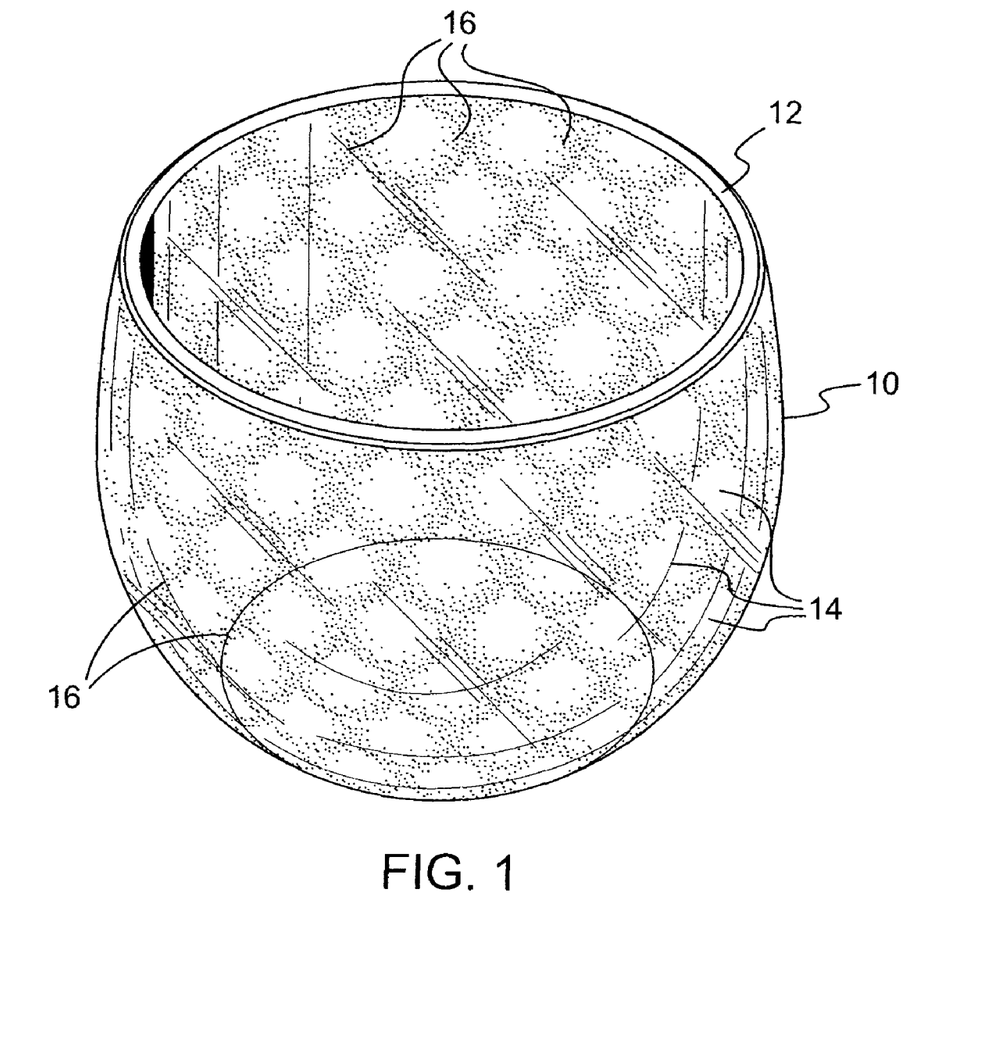
FIG. 1 is a perspective view of a candle holder according to our invention.
Figure 2:
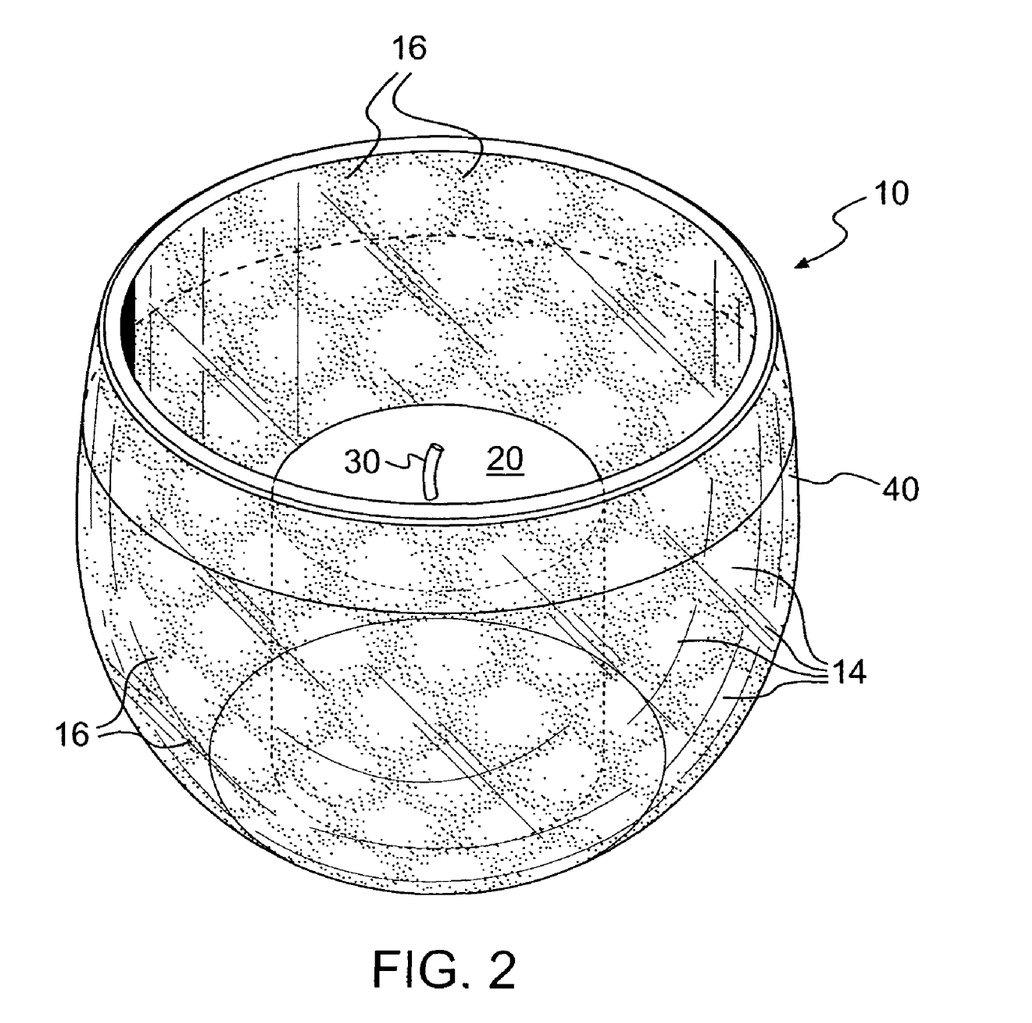
FIG. 2 is a perspective view of the candle holder holding a free-standing candle according to our invention.
Figure 3:
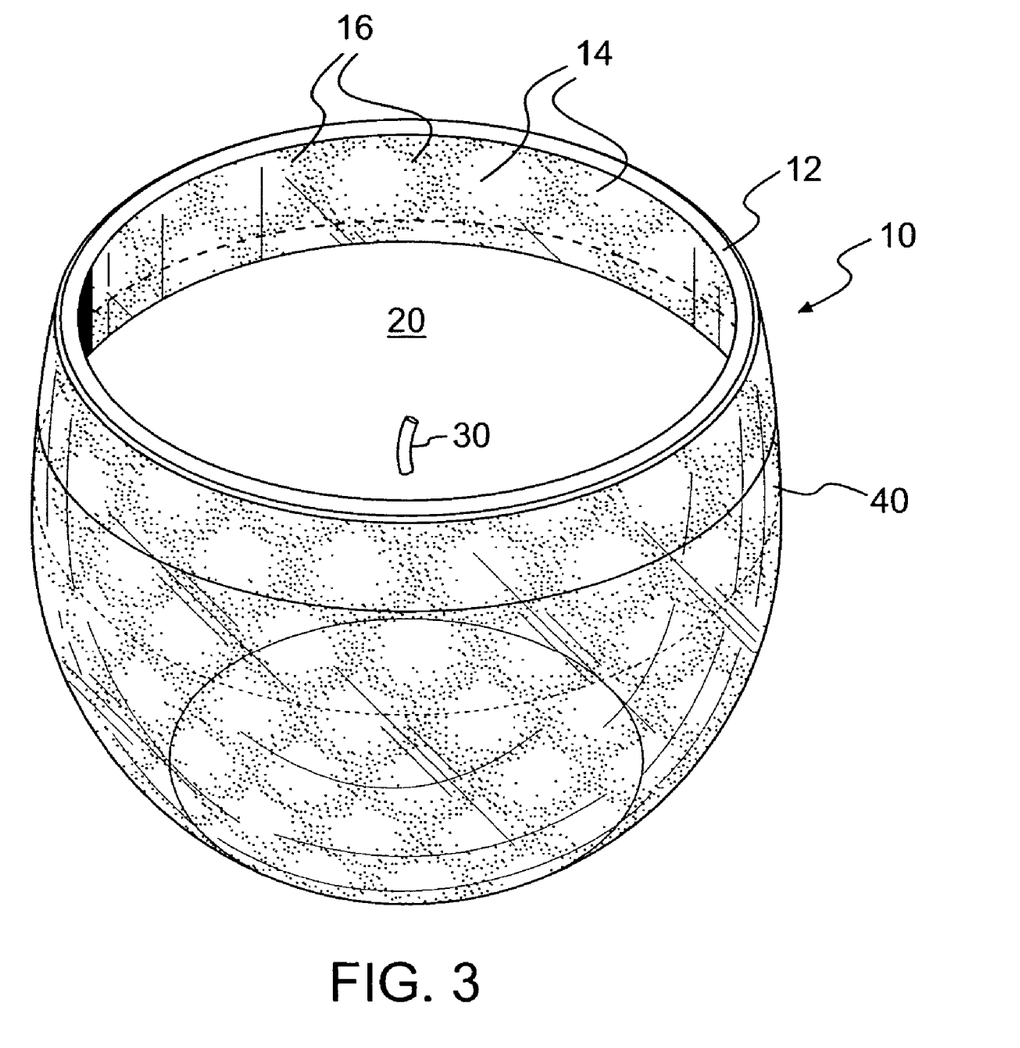
FIG. 3 is a perspective view of the candle holder with a poured-in candle disposed therein.

As shown in FIGS. 1 through 3, our invention comprises a candle holder 10 preferably filled with a combustible material 20, such as wax, through which a wick 30 is provided to create a candle. The combustible material 20 and wick 30, in the form of a candle, may be free standing as shown in FIG. 2, or poured in as shown in FIG. 3. In either case, the top surface of the combustible material is disposed below the upper rim 12 of the candle holder 10, such that when the wick 30 is lit, thereby burning the combustible material 20 via the wick 30 and generating a continuous flame about the wick 30, light emanating from the flame is refracted by at least the portion of the candle holder 10 extending between the top surface of the combustible material 20 and the upper rim 12.

As shown schematically in FIGS. 1 through 3, the candle holder 10 includes an inner surface having a hammered texture (such hammered texture need not resemble the regular pattern depicted in these figures, and preferably is substantially irregularly patterned as shown, for example, in FIG. 4). As previously discussed, we understand the term "hammered," as used to describe the texture of a surface, to be a term of art in at least, for example, the glass art and industry. For instance, "hammered" means glass textured by indentations which resembles a surface that has been beaten with a ball-peen hammer, or a surface texture similar to hammered brass or copper, that is, a texture having small, round-like, substantially smooth bumps. Within this meaning of hammered and according to an embodiment of our invention, the hammered surface preferably is created by way of a variation in thickness of the candle holder so as to provide a visual impression that the surface has been subjected to a treatment resulting in changes of thickness of the candle holder and creating a surface that appears to have been subjected to a hammering operation, or an appearance similar to a surface that has been imperfectly smoothed by being hammered.

Although the hammered texture schematically shown in FIGS. 1 through 3 appears to have a substantially regularly repeating pattern, the hammered texture is preferably irregularly patterned. Of course, a regular pattern may be used, provided the resulting texture is a "hammered" texture as previously explained above.

Although the inner surface preferably has the hammered texture, the hammered texture may be applied to the outer surface of the candle holder 10.

As shown in FIGS. 1 through 3, the hammered inner surface of the candle holder preferably comprises a plurality of substantially round forms 14, which appear to have been formed by a hammer hitting the surface, bounded by a substantially continuous vein 16, which was not hit by the hammer (or was not hit as hard or as often).

Most preferably, the continuous vein 16 is a depression or relative thinness bounding a plurality of substantially rounded mounds 14 or relative thickness. Each of the mounds 14 generally extends towards the center of the candle holder so that from the viewpoint of the center of the candle holder each mound has a substantially convex appearance.

The hammered effect may also comprise the mirror image of the above-described vein 16 and mounds 14, such that the vein 16 extends inward so the wall of the candle holder 10 is relatively think at the vein 16, while the substantially rounded forms 14 are substantially concave so the wall of the candle holder is relatively thin at the forms 14.

The candle holder is preferably provided with the irregular inner surface during manufacture, such as when the glass is still soft and malleable. (By inner surface, we mean to refer to the surface of the chimney, holder, or jar closest to the candle flame or light source during burning of the candle, and by the term outer surface, we mean to refer to the surface upon which the decorative heat-shrinkable film, if any, is applied.)

While it is possible to obtain a pleasing effect by the use of striations, cuts, ridges, or other decorative patterns in the inner surface of the candle holder, we have found that the use of the aforementioned hammered texture is the most pleasing. Moreover, such hammered texture is most easily achieved during molding of the glass, particularly in the case of a glass candle jar.

Various embodiments of a decorated luminary product may be formed in accordance with our invention. In one embodiment, shown in FIGS. 2 and 3, the luminary product is preferably decorated by enveloping an outer surface in a decorative, heat-shrinkable polymer film or web 40 and heat-shrinking the web 40 about the surface to cause it to adhere tightly thereto. However, as will be evident to one skilled in the art, the decorative webs used in the present decorated luminary product may be applied by such alternative means as attachment with holding devices such as staples, pins, tape, etc., or by adhesive or static electricity. At any rate, the heat-shrinkable web 40 has decorative features, such as ink applied thereon, to form figures or characters, or coloring, or other features having aesthetic functions. These features, being on the heat-shrinkable web 40 which is applied to the outer surface of the candle holder 10, are located to cooperate with light emitted by the candle 20 to augment the visual effect of the luminary product when the candle 20 is lit.

The present invention may be modified to be used with various configurations of globes or lantern chimneys, usually made of glass, designed to surround, enclose, encompass, retain, or hold candles of various shapes, oil burning lamps or various wicks which burn carbon-based fuel.

While the use of transparent globes, chimneys, or candle containers (such as jars) is preferred, it is possible to use translucent materials as well, although the visual effect is usually not as pronounced in such a case.

The present invention is also particularly applicable to candle holders, oil lamps, and the like that include a luminary element, such as a candle, that dispenses an active material. Such active materials are well known in the prior art, and may be selected from the group consisting of fragrances, air fresheners, deodorizers, odor eliminators, malodor counteractants, insecticides, insect repellants, medicinal substances, disinfectants, sanitizers, mood enhancers, aroma-therapy compositions, and mixtures thereof. The choice of specific active materials present in the luminaries of our invention, if any, are within the skill of a practitioner of the art to which our invention applies. However, preferred active materials which may be included in the wax of a candle, or in the oil of an oil burning lamp, include fragrances, insect repellants, insecticides, and deodorizers. Such active materials may be added, in liquid or gel form, to the fuel element of a candle or lamp to be dispersed to the atmosphere upon burning of the fuel.

The invention may also be used with heat-shrinkable webs on the outer surface of the candle holder having printing in thermochromatic inks. The web is preferably in a position such that the thermochromatic ink may be illuminated and heated by the flame of the luminary product when lit, and react thermochromatically so as to change before the viewer when the flame is burning, and possibly, after the flame is extinguished. The thermochromatic ink may also absorb heat energy from the atmosphere when the flame of the luminary is unlit.

The thermochromatic feature can be provided by means of a heat-shrinkable web bearing the ink, the web being preferably adhered to the outer surface of the luminary product in such a manner as to be illuminated and heated by the flame thereof, or alternatively, heated by the ambient atmosphere when the luminary flame is unlit. The web changes color when the web is exposed to a temperature above an activation temperature for the ink, such as after the burning element is lit, and if a reversible thermochromatic ink is employed, for a time after the flame is extinguished. Such reversible thermochromatic inks return to their original color after cooling to or near to room temperature.

It is to be understood that the heat energy necessary to excite or to change the thermochromatic material used in our invention includes not only ambient heat, including heat from external sources such as furnace heating, a fireplace in a home, or sunlight, but also includes the heat released by a flame burning at the wick of a candle, or on the wick of an oil lamp, or other such sources. The webs employed are applied by heat shrink techniques to substrates such as candle jars, globes, votive jars, and chimneys, to provide a decorative luminary product.

The thermochromatic inks may be any suitable inks for imprinting upon a heat-shrinkable film. The specific ink or pigmentation selected should be compatible with the shrink wrap film to which it is to be applied, and any nonthermochromatic or phosphorescent inks to be utilized in conjunction therewith, and should be capable of exhibiting a thermochromatic response to the heat of a burning luminary at the distance at which a heat-shrinkable web or film shall be positioned from the flame of the burning luminary. The thermochromatic response to the heat may take the form of a change in color, a change from colored to transparent and colorless, or a change from transparent and colorless to colored. Essentially any thermochromatic change visible to the eye may be of interest with respect to use in our invention, particularly those that are reversible.

A preferred embodiment of the invention comprises a heat-shrinkable web having a clear film background with a colored design or indicia imprinted thereupon, applied to a transparent glass candle holder, in such a manner that the design or indicia is backlit by the flame of the candle during burning, and absorbs radiant energy from the flame while it burns. After a period of burning and absorption of heat from the flame, the thermochromatic ink in the printed design or indicia changes from transparent to a color, or changes color, showing the design or indicia in sharper contrast to the background, while other portions of the film, not printed in thermochromatic inks, do not change. By printing the heat-shrinkable film with a plurality of colored thermochromatic inks, either in single pass printing processes, or in multiple applications of different inks, complex multi-colored designs may be obtained, which will absorb light and heat from the candle while the candle burns, as well as from any ambient heat, and change color to provide a pattern of multiple colors, where there had previously been a transparent area or an area of limited coloration.

For example, a heat-shrinkable web according to our invention may be printed in a conventional manner with a design of a flower, with the leaves printed in a thermochromatic ink which changes when heated from transparent to green, while a flower bud and petals may be printed in an ink which changes upon heating from transparent to red. After burning of the candle for a few minutes, the image of a flower is seen on the candle holder, where previously it had been substantially undetectable.

Other inks, such as phosphorescent inks, may also be used to decorate the heat-shrinkable film. Exemplary of such inks are those prepared from Luminous Glow Powder sold under the tradename HY-Series Luminous Material, available from Pete's Luminous Creations, of Singapore. Such phosphorescent materials are based upon a non-radioactive crystal which is available in green, blue, yellow, and violet, in particle sizes of 200 to 500 mesh. The 200 mesh size is suitable for most applications except silk screen printing, or offset printing, where a finer particle size of 400 to 500 mesh is recommended. The crystals of this composition decompose in water, and accordingly must be applied as non-aqueous dispersions, such as solvent based inks. The Glow Powder may be mixed with suitable clear inks to form Luminous Inks. The mixing ratio of powder and ink is approximately 1:1, but generally speaking, the luminescence is greater with higher proportions of luminous material present, and when more than one coating of ink is applied. Application to a clear or white film is preferred, since a dark background tends to absorb light and reduce luminescence. The Glow-in-the-Dark Powder may also be utilized to form an epoxy coating by combination with Epoxy, Hardener, and powder. Other glow-in-the-dark materials are also available commercially, such as phosphorescent pigments sold by Thermal Lettering, of Loveland, Colo.

Application of the phosphorescent pigment or ink to a heat-shrinkable film may be done by any appropriate means, including painting, application by rubbing or contacting the surface with the pigment or ink, or by printing, such as by flexography, gravure, or screen printing, with screen printing being preferred.

The heat-shrinkable web applied to the candle holder of our invention may have other properties independent of any ink printed thereon, such as birefringence. A birefringent, reflective, color-altering, heat-shrinkable web for application to the candle holder may be based on a film as commonly referred to as a mirror film, available from 3M, of St. Paul, Minn. Such films comprise alternating layers of at least two differing polymers, the film transmitting substantially all incident visible light at approximately a zero degree observation angle, and transmitting substantially all visible light except a selected portion of the spectrum at at least one observation angle greater than a predetermined shift angle. Thus, the film may appear to be clear, i.e. to be transparent, or to exhibit one color when observed at a zero degree observation angle, and to exhibit a different visible color when viewed at an observation angle greater than some predetermined angle.

As set forth in U.S. Pat. No. 6,045,894, an exemplary color shift from clear to cyan is produced by creating a multilayer film including multiple polymeric layers selected to enable the film to reflect light in the near infrared portion of the visible spectrum at zero degree observation angles, and to reflect red light at angles greater than the "shift" angle, which is that angle, measured relative to an optical axis extending perpendicular to the film, at which the film first appears colored. Depending upon the amount and range of red light reflected, the film may exhibit a visible color, commonly cyan. Thus, one viewing from the zero observation angle will see through the film while one viewing at the shift angle, or at an angle greater than the shift angle, will see a cyan-colored film.

The heat-shrinkable web can be a polymeric material having properties such as to provide the desired properties of our invention. That is, the heat-shrinkable web constitutes a film upon which is deposited an image incorporating, for example, a thermochromatic ink either in a random manner, or in a desired pattern, which ink will be "changed" or radiantly heated by the incidence of light from a flame at the wick of the associated candle, and which will react in response thereto. As indicated, the thermochromatic or phosphorescent ink or birefringent film may take a pattern, such as a drawing, an image, a print indicia, or the like, or may be a totally random "splash" of coloration, either in a single color, or in a combination of colors.

For example, the heat-shrinkable web may be provided with a design that should not only improve the appearance of the candle holder, but should cooperate with light emitted by the candle to augment the visual effect created when the candle is burning. For example, the base heat-shrinkable web may be colored and translucent. This will augment any surface features (e.g., fillets, flutes, or the hammered texture) of the candle holder in a similar manner as would tinted glass. Alternatively, the heat-shrinkable web may be selectively transparent and/or translucent and may even have portions that are opaque, in order to provide a desired light pattern when the candle is lit. The design can be provided by any of a number of suitable processes, such as printing (including using conventional inks throughout, or in selected areas) or finishing (including providing gloss, matte, or other specialty finishes).

We have found that the preferred heat-shrinkable film material, poly(ethylene terephthalate) (PET), withstands the expected conditions (e.g., extended exposure to temperatures of up to about 65.6° C. (150° F.)) of use, and performs acceptably when exposed to such non-standard conditions as flare-ups (during which temperatures can approach about 315° C. (600° F.) to 427° C. (800° F.)), misalignment, and the like. Although this material is preferred, the heat-shrinkable film material may be any of a number of suitable heat-shrinkable polymer films, including PVC, polyethylene, polystyrene, other polyesters, and the like, so long as the film is not adversely affected by the temperatures encountered during normal candle use.

Further, we prefer that the film be heat-shrinkable at sufficiently low temperatures or brief exposure times so that the candle itself, if present within the candle holder, will experience little or no melting during the shrinking process.

It has also been noted that additional aesthetic improvement may be achieved by the use of multiple wax colors in the candle placed in the candle holder of our invention, so as to provide variance in the color of the candle as observed both when burning and when unlit.

The decorating process for the wrapped-holder includes the step of providing a web of heat-shrinkable film. The design or pattern desired is printed, drawn, painted, or otherwise applied to the surface of the film prior to the web being affixed to the luminary product. The design is preferably applied by printing or by similar appropriate application means, using appropriate decorative inks. It is possible for the design to comprise conventional, phosphorescent and glow-in-the-dark design elements, and thermochromatic elements so that differing designs show in the presence and absence of either candle light and heat or ambient lighting and heat.

Preferably, but not necessarily, the web will be provided in individual pieces, such as preformed, closed loops or bands that fit over or encircle a candle holder, or panels that are wrapped about a candle holder. The step of providing the web can include the steps of providing a continuous sheet and severing the sheet into the individual panels, or providing a continuous sleeve and severing the sleeve into the individual bands. The design on the web preferably will be applied to the film before it is severed into individual panels or bands.

In any case, the edges of the web are overlapped and seamed in a known manner, either before (in the case of bands) or after (in the case of panels) application to the candle holder. For example, the edges may be solvent sealed, heat sealed, adhesively sealed, sonically welded, or the like. In the case of bands, the edges are joined during the formation of the bands, which in a preferred embodiment is done by joining opposing edges of the film by tetrahydrofuran (THF) solvent applied in a known manner.

The web may be oriented so as to shrink predominantly in a single direction, thereby improving the predictability of the shrink-wrapping process. This can be accomplished in a known manner. For example, prior to formation of the individual panels or bands, the web can be heated and stretched in one direction. Usually this will be done in the cross-machine direction (transverse to the length of the web). When the web is heated again later, in a heat-shrinking process, the web will shrink predominantly in the direction in which it has been stretched. Although not necessary to the invention, it would be preferable to orient the web so as to shrink about the candle holder to a much greater extent in the circumferential rather than the axial direction. This facilitates orientation of the web relative to the candle holder. The not-yet-shrunk web can be placed about the candle holder, by encircling or wrapping, and the top or bottom edge of the film can be aligned substantially with its intended final position. As the web shrinks (predominantly circumferentially), the web will close tightly about the candle holder without undue axial displacement of the top and bottom edges of the web.

The decorative web is located or positioned about the candle holder so as to cooperate with light emitted by the candle in the candle holder to augment the visual effect when the candle is lit. Such proper location is ensured when at least a portion of the decorative web extends above a top surface of the candle, for example. This allows light from a burning candle, for example, to pass through at least a portion of the decorative web, preferably for the life of the burning candle.

The preferred PET film is about 25 to about 60 microns thick, preferably 50 microns thick, and is oriented transversely so as to exhibit the following shrinkage characteristics when submersed in heated water for fifteen minutes:

| Water | Shrinkage (%) | |
| --- | --- | --- |
| Temperature (° C.) | Machine direction | Cross-machine direction |
| 80 | <4 | 50–60 |
| 100 | <3 | >70 |

The individual bands or panels for application to each candle holder can be produced by severing the continuous sleeve or sheet at a timing metered by the output of a photosensor. The photosensor can be employed to detect predetermined registration markers on the sleeve or sheet, in order to ensure that the sleeve or sheet is severed at appropriate intervals with respect to the design on the web. (If desired, the photosensor detection "window" can be limited to specified time periods in a known manner.) If the decorative design is a repeating pattern, then the photosensor can key on a specific aspect of the pattern. If the design is not repeating or repeats less frequently than every cutting interval, then a standard registration marker can be provided.

For example, a clear box with a specified border can be incorporated into each design at the same location in the individual bands or panels. This permits a continuous sleeve or sheet to bear more than one design resulting in bands or panels that differ from one another in design. This greatly increases the ease and cost-effectiveness of producing luminary products decorated with varied designs, particularly bearing a plurality of thermochromatic inks or overlapping designs.

The candle holder is preferably encased by the heat-shrinkable film. In the preferred embodiment, this is done with an encircling band or wrapped panel that is slightly larger in circumference than the target candle holder. In the case of, for example, a candle holder that is not cylindrical (i.e., it is wider in some places than others), the encircling band or wrapped panel should be slightly larger in circumference than the widest part of the candle holder. This, however, is not always necessary, since the band or panel can be stretched onto a slightly larger candle holder if desired.

The height of the band or panel can be close to the desired height of the finished design on the candle holder. As noted, an oriented web can be used in a known manner to provide a band that shrinks predominately in the circumferential direction, with very limited shrinkage in the axial direction.

A typical band will be described for application to a curved candle holder, i.e. a candle jar, that is approximately 68.6 mm tall and has a side wall that is approximately 70.6 mm in diameter at its mouth, bulges to approximately 80.8 mm in diameter (approximately 253.8 mm in circumference) at its widest point, and tapers to approximately 40.5 mm in diameter at its base. The elongated sleeve, from which the bands are formed, is approximately 260.75 mm in circumference (corresponding to approximately 83.0 mm in diameter). The sleeve is severed transversely into bands that are approximately 71.0 mm in height. Thus, each band is approximately 7.0 mm larger in circumference than the holder. Each band is also approximately 2.4 mm taller than the holder. However, due to the bulged side wall of the holder, the actual distance along the side wall from top to bottom actually exceeds the height of the band by a few millimeters.

The thus-formed band is then placed over the candle holder, thus encasing and encircling the candle holder. At this stage of the process for wrapping a candle holder, it is preferred that no candle be present, although this is not necessary to the invention. This permits the candle holder to be oriented upside-down on a carrying surface (such as a conveyor belt or tray) for band application. This provides several advantages. In this orientation, the band can rest against the carrying surface at the outset of heat-shrinking. This prevents the web from overlapping the mouth of the holder. It also provides a reference surface to keep the web from skewing relative to the holder. A secondary advantage is that the absence of the candle at this stage avoids subjecting the candle to the elevated temperatures of the heat-shrinking process, which could result in some softening or melting (although the melting can be kept to a minimum).

It should be noted that the candle may be positioned in the candle holder earlier in the process, and may be present before the web is applied to the candle holder. For example, in the case of gel-candles or pour-in-wax candles, the candle may be poured into the candle holder at any point in the process. In fact, it is possible that the candle may be at such a temperature when poured into the candle holder that the candle itself can contribute to or achieve the heating step (discussed below).

Once the band or panel is positioned about the candle holder, the combination can be fed by any known mechanism (e.g., a conveyor belt) into a heating station, where the band or panel is heat shrunk onto the candle holder. The heating station can apply hot, dry air; hot, humid air or steam; or some sequential combination of hot air and steam. The sequential combination is preferred in order to best avoid wrinkles and bubbles in the finished web, in a manner well known in the art. However, it is to be noted that additional interesting and varying visual effects may be obtained by allowing the formation of wrinkles and bubbles in the web as applied to the candle holder. For example, such irregularities add visual depth and variation to the product, and a three-dimensional effect is possible. In the case of a PET film having the above-noted thickness and shrinkage characteristics, formed into bands having the above-noted dimensions, and having a design printed thereupon, the bands are subjected to four consecutive stations of hot, dry air (about one to about two seconds each at a temperature of about 37.8° C. (100° F.) to about 151° C. (400° F.), preferably about 113° C. (300° F.) to about 151° C. (400° F.), depending on application), and then to a station of steam (about three to about five seconds at a pressure of about 34.4 kPa (5 psi) to about 103 kPa (15 psi.)).

The number, order, exposure time and intensity of the heating stations can be varied in a known manner according to the specific dimensions and characteristics of the heat-shrinkable web and the candle holder.

Once heat-shrinking is complete, the wrapped candle holder may be dried if necessary by a conventional air blow-dryer or other known mechanism, at which point the luminary product is ready for packaging once the candle is positioned therein.

A luminary product, comprising a small jar candle, having an inner surface bearing a hammered texture, and having a decorative web attached to the outer surface of the jar, was prepared in accordance with the methods set forth above. A film of poly(ethylene terephthalate) (PET) shrink wrap material was cut to fit a jar candle similar to those such as sold under the trademark Glade® Candles, commercially available from S.C. Johnson & Son, Inc., of Racine, Wis., but differing from such jars by the presence of the hammered inner surface. A design was printed on the film to form a web, the web was applied to the outer surface of the jar candle in the manner set forth above, and shrunk to a tight fit thereupon. The unlit jar candle was observed, and the design was found to show a variation in shapes and color intensities as the angle of observation was changed. After being lit, and after having burned for about fifteen minutes, the luminary product was again observed. This time, the design appeared as before, but with additional variation in design and color as the candle flickered. After the candle was extinguished and allowed to cool to room temperature, the design appeared as originally observed.

Although the above-described process is preferred, alternative processes may be used. For example, alternative methods utilizing a preformed loop of film are described in the above-noted Spiegel, et al. patent (in which the loop fits loosely over the object before heat-shrinking). An alternative method utilizing a sheet that is wrapped around the object is described in U.S. Pat. No. 5,879,496 (Bright, et al.).

We have found that our invention provides an additional advantage in that the heat-shrinkable film, when applied, protects the candle holders, which are typically glass. Specifically, the heat-shrinkable film maintains the integrity of and otherwise protects the glass, especially the glass having the hammered texture, during production or use from, for example, abrasion or scratching. Glass, once scratched, loses compression strength and becomes more fragile. The heat-shrinkable film reduces the incidents of such abrasion or scratching, and preserves the integrity of the glass.

While our invention has been described with respect to what is at present considered to be the preferred embodiments, it should be understood that the invention is not limited to the disclosed embodiments. To the contrary, the invention is intended to cover various modifications and equivalent arrangements, some of which are discussed above, included within the spirit and scope of the appended claims. Therefore, the scope of the following claims is intended to be accorded the broadest reasonable interpretation so as to encompass all such modifications and equivalent structures and functions.

INDUSTRIAL APPLICABILITY

The inventive decorative luminary product uses a luminary element, a luminary element holder having a hammered texture formed on an inner surface of the holder, and a heat-shrunk decorative web encased about the holder to produce an augmented and pleasing visual effect. The hammered texture cooperates with the light emitted by the luminary element, such as a candle, to achieve the pleasing visual effect, greatly enhancing the aesthetics of the decorative luminary product during the burning of the luminary element.

We claim:

1. A decorated luminary product comprising:
   a candle;
   a candle holder containing said candle, said candle holder having an inner surface and an outer surface; and
   a web of a heat shrunk polymer encasing the outer surface of said candle holder, said web including a decorative feature,
   wherein the inner surface of said candle holder has a hammered texture and the decorative feature of said web is located so as to cooperate with light emitted by said candle in said candle holder to augment a visual effect when said candle is lit.

2. A decorated luminary product comprising:
   a candle;
   a candle holder containing said candle, said candle holder having an inner surface and an outer surface; and
   a web of a heat shrunk polymer encasing the outer surface of said candle holder, said web including a decorative feature,
   wherein at least one of the inner surface and the outer surface of said candle holder has a hammered texture, the decorative feature of said web is located so as to cooperate with light emitted by said candle in said candle holder to augment a visual effect when said candle is lit, and the hammered texture causes differing refraction of light emitted from said candle when lit.

3. A decorated luminary product according to claim 1, wherein said candle comprises a plurality of colors.

4. A decorated luminary product according to claim 1, wherein said candle includes an active material.

5. A decorated luminary product according to claim 4, wherein said active material is selected from the group consisting of fragrances, air fresheners, deodorizers, odor eliminators, malodor counteractants, insecticides, insect repellants, medicinal substances, disinfectants, sanitizers, mood enhancers and aroma-therapy compositions.

6. A decorated luminary product according to claim 1, wherein the decorative feature of said web includes one of a thermochromatic ink and a phosphorescent ink.

7. A decorated luminary product according to claim 1, wherein said web is applied onto said candle holder such that wrinkles and bubbles are formed in said web.

8. A decorated luminary product comprising:
   a candle;
   a candle holder containing said candle, said candle holder having an inner surface and an outer surface; and
   a web of a heat shrunk polymer encasing the outer surface of said candle holder, said web including a decorative feature,
   wherein at least one of the inner surface and the outer surface of said candle holder has a hammered texture, the decorative feature of said web is located so as to cooperate with light emitted by said candle in said candle holder to augment a visual effect when said candle is lit, and said web exhibits birefringence.

9. A decorated luminary product comprising:
   a candle;
   a candle holder selected from the group consisting of chimneys, globes and jars, containing said candle, said candle holder having an inner surface and an outer surface; and
   a web of a heat shrunk polymer encasing said candle holder, said web including a decorative feature,
   wherein the inner surface of said candle holder has a hammered texture and the decorative feature of said web is located so as to cooperate with light emitted by said candle in said candle holder to augment a visual effect when said candle is lit.

10. A decorated luminary product according to claim 9, wherein said candle holder comprises one of glass and plastic.

11. A decorated luminary product according to claim 9, further comprising a wick-based, hydrocarbon-fuel-burning candle.

12. A decorated luminary product according to claim 9, wherein the decorative feature of said web includes one of a thermochromatic ink and a phosphorescent ink.

13. A decorated luminary product comprising:
    a candle;
    a candle holder selected from the group consisting of chimneys, globes and jars, containing said candle, said candle holder having an inner surface and an outer surface; and
    a web of a heat shrunk polymer encasing said candle holder, said web including a decorative feature,
    wherein at least one of the inner surface and the outer surface of said candle holder has a hammered texture, the decorative feature of said web is located so as to cooperate with light emitted by said candle in said candle holder to augment a visual effect when said candle is lit, and said web exhibits birefringence.

14. A decorated luminary product according to claim 9, wherein said web is applied onto said candle holder such that wrinkles and bubbles are formed in said web.

15. A luminary product comprising:
    a combustible material;
    a glass jar containing said combustible material, said combustible material having been poured into said glass jar, said glass jar having an inner surface and an outer surface;
    a web of a heat shrunk polymer encasing the outer surface of said glass jar; and
    a wick extending through said combustible material,
    wherein the inner surface of said glass jar has a hammered texture such that light passing through said glass jar varies substantially as a result of variation of refraction of the light.

16. A luminary product comprising:
    a combustible material;
    a glass jar containing said combustible material, said combustible material having been poured into said glass jar, said glass jar having an inner surface and an outer surface;
    a web of a heat shrunk polymer encasing the outer surface of said glass jar; and
    a wick extending through said combustible material,
    wherein (i) at least one of the inner surface and the outer surface of said glass jar has a hammered texture such that light passing through said glass jar varies substantially as a result of variation of refraction of the light, and (ii) said glass jar includes an upper rim forming an upper boundary of said glass jar and a top surface of said combustible material is disposed below said upper rim such that when said wick is lit, thereby burning said combustible material via said wick and generating a continuous flame about said wick, light emanating from the flame is refracted by at least a portion of said glass jar extending between said top surface of said combustible material and said upper rim.

17. A luminary product comprising:
    a combustible material;

a glass jar containing said combustible material, said combustible material having been poured into said glass jar, said glass jar having an inner surface and an outer surface;

a web of a heat shrunk polymer encasing the outer surface of said glass jar; and a wick extending through said combustible material, wherein (i) at least one of the inner surface and the outer surface of said glass jar has a hammered texture such that light passing through said glass jar varies substantially as a result of variation of refraction of the light, and (ii) said web of heat shrunk polymer exhibits birefringence.

18. A luminary product comprising:

a combustible material;

a glass jar containing said combustible material, said combustible material having been poured into said glass jar, said glass jar having an inner surface and an outer surface;

a web of a heat shrunk polymer encasing the outer surface of said glass jar; and a wick extending through said combustible material, wherein (i) at least one of the inner surface and the outer surface of said glass jar has a hammered texture such that light passing through said glass jar varies substantially as a result of variation of refraction of the light, and (ii) the hammered texture causes differing refraction of light when said wick is lit.

19. A luminary product according to claim 15, wherein said combustible material has a plurality of colors.

20. A luminary product according to claim 15, wherein said combustible material includes an active material.

21. A luminary product according to claim 20, wherein said active material is selected from the group consisting of fragrances, air fresheners, deodorizers, odor eliminators, malodor counteractants, insecticides, insect repellants, medicinal substances, disinfectants, sanitizers, mood enhancers and aroma-therapy compositions.

22. A luminary product according to claim 15, wherein said web of heat shrunk polymer includes a decorative feature.

23. A luminary product according to claim 22, wherein the decorative feature of said web includes one of a thermochromatic ink and a phosphorescent ink.

24. A decorated luminary product according to claim 22, wherein said web is applied onto the outer surface of said candle holder such that wrinkles and bubbles are formed in said web.

* * * * *